(12) United States Patent
Mealing et al.

(10) Patent No.: US 10,933,204 B2
(45) Date of Patent: Mar. 2, 2021

(54) PRESCRIPTION BOTTLE CAP CAPABLE OF ADMINISTERING OPIOID OVERDOSE REVERSAL AGENT

(71) Applicant: CounterAct, LLC, Heber City, UT (US)

(72) Inventors: Donald Roy Mealing, Heber City, UT (US); Todd David Pizitz, Vista, CA (US)

(73) Assignee: CounterAct, LLC, Heber City, UT (US)

(*) Notice: Subject to any disclaimer, the term of this patent is extended or adjusted under 35 U.S.C. 154(b) by 264 days.

(21) Appl. No.: 15/993,449

(22) Filed: May 30, 2018

(65) Prior Publication Data
US 2019/0134319 A1    May 9, 2019

Related U.S. Application Data

(60) Provisional application No. 62/513,768, filed on Jun. 1, 2017.

(51) Int. Cl.
*A61M 11/00* (2006.01)
*A61M 15/08* (2006.01)
(Continued)

(52) U.S. Cl.
CPC .............. *A61M 11/007* (2014.02); *A61J 1/06* (2013.01); *A61J 1/062* (2013.01); *A61J 1/1412* (2013.01);
(Continued)

(58) Field of Classification Search
CPC .. A61M 11/007; A61M 11/008; A61M 11/00; A61M 11/006; A61M 15/0003; A61M 15/0021; A61M 15/0025–0026; A61M 15/003; A61M 15/0023; A61M 15/004; A61M 15/08; A61J 1/1425; A61J 1/06; A61J 1/067; A61J 1/1412; B05B 11/3009; B05B 11/3011; B05B 11/3012;
(Continued)

(56) References Cited

U.S. PATENT DOCUMENTS

| 5,011,032 A | 4/1991 | Rollman |
| 5,307,953 A * | 5/1994 | Regan ............... A61M 15/0028 222/82 |
| 5,484,089 A | 1/1996 | Picerno |
| 5,771,657 A | 6/1998 | Lasher et al. |

(Continued)

OTHER PUBLICATIONS

International Search Report and Written Opinion from PCT International Application No. PCT/US18/35208, dated Aug. 30, 2018, 14 pages.

*Primary Examiner* — Justine R Yu
*Assistant Examiner* — Kelsey E Baller
(74) *Attorney, Agent, or Firm* — Dentons Durham Jones Pinegar

(57) ABSTRACT

An apparatus for delivering a therapeutic agent may be associated with a cap for a bottle that contains a prescription for a drug to which the therapeutic agent corresponds. When the prescription bottle holds an opioid, the therapeutic agent may be a substance that counteracts the effects of the opioid. The apparatus may include a nozzle that facilitates nasal administration of the therapeutic agent. The apparatus may be capable of attaching to a cap for a prescription bottle, or the apparatus may have a configuration that enables it to serve as the cap for the prescription bottle.

17 Claims, 7 Drawing Sheets

(51) Int. Cl.
*A61J 7/00* (2006.01)
*A61M 15/00* (2006.01)
*A61J 1/14* (2006.01)
*A61J 1/06* (2006.01)

(52) U.S. Cl.
CPC .......... *A61J 1/1425* (2015.05); *A61J 1/1475* (2013.01); *A61J 7/0053* (2013.01); *A61M 11/008* (2014.02); *A61M 15/0003* (2014.02); *A61M 15/004* (2014.02); *A61M 15/0023* (2014.02); *A61M 15/0036* (2014.02); *A61M 15/08* (2013.01); *A61M 2210/0618* (2013.01)

(58) Field of Classification Search
CPC ............ B05B 11/3014; B05B 11/3015; B05B 11/3046; B05B 11/3056; B05B 11/3057; B05B 11/0027; B05B 11/3059; B65D 83/22; B65D 51/28; B65D 51/247
USPC ............ 128/200.14, 200.23, 203.12, 203.15, 128/200.19
See application file for complete search history.

(56) References Cited

U.S. PATENT DOCUMENTS

| | | | | |
|---|---|---|---|---|
| 5,901,703 A * | 5/1999 | Ohki | ................. | A61M 15/0033 128/203.12 |
| 6,145,703 A * | 11/2000 | Opperman | ........ | A61M 15/0065 222/82 |
| 6,186,141 B1 * | 2/2001 | Pike | ................... | A61B 18/1206 128/203.12 |
| 6,302,295 B1 | 10/2001 | Weisman | | |
| 6,715,649 B2 * | 4/2004 | Santagiuliana | ..... | B05B 11/0094 222/380 |
| 6,959,708 B1 * | 11/2005 | Rasor | ..................... | A61K 31/21 128/203.12 |
| 2002/0074429 A1 * | 6/2002 | Hettrich | .............. | B05B 11/0044 239/333 |
| 2006/0207596 A1 * | 9/2006 | Lane | .................... | A61M 11/007 128/206.11 |
| 2010/0100237 A1 | 4/2010 | Ratnakar | | |
| 2011/0147404 A1 | 6/2011 | Dobie, III | | |
| 2016/0008277 A1 | 1/2016 | Crystal et al. | | |
| 2016/0311588 A1 * | 10/2016 | Wochele | ............ | B65D 51/1616 |

* cited by examiner

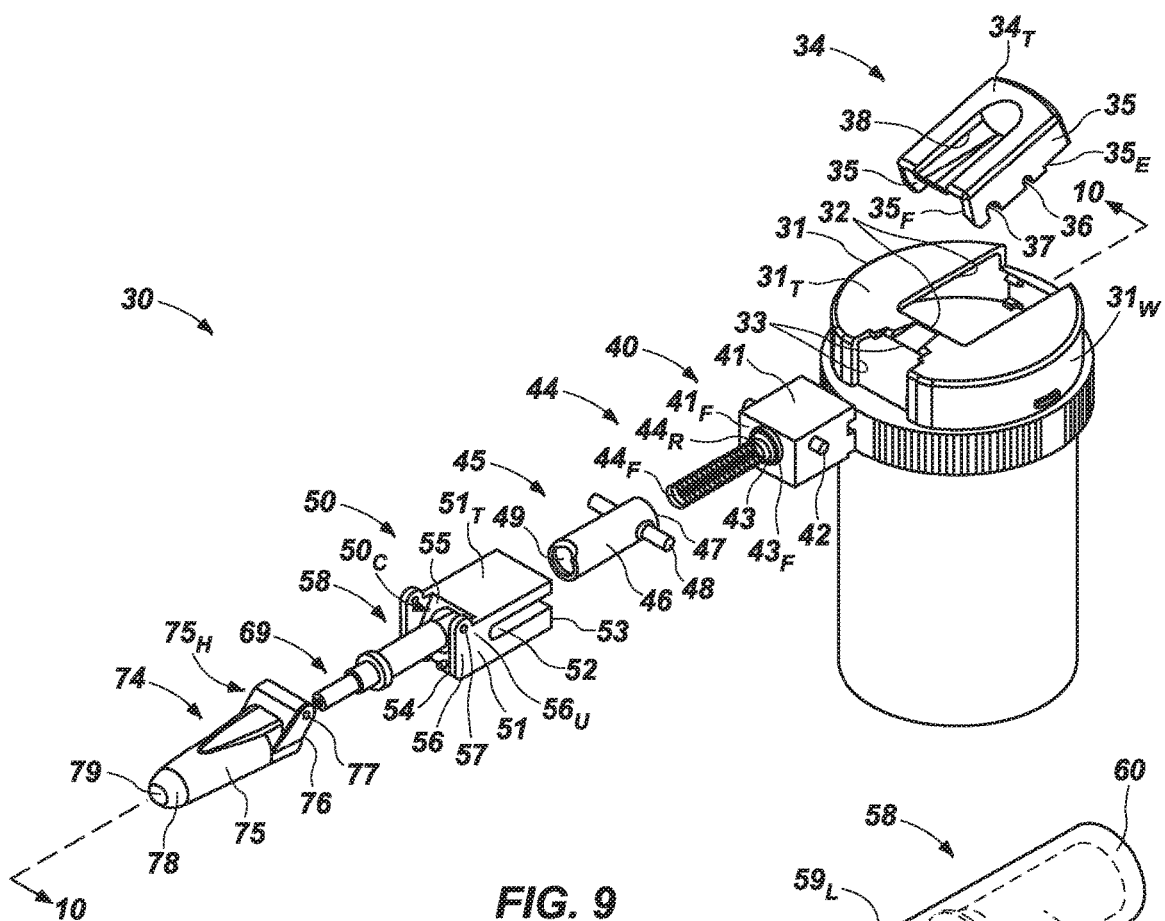
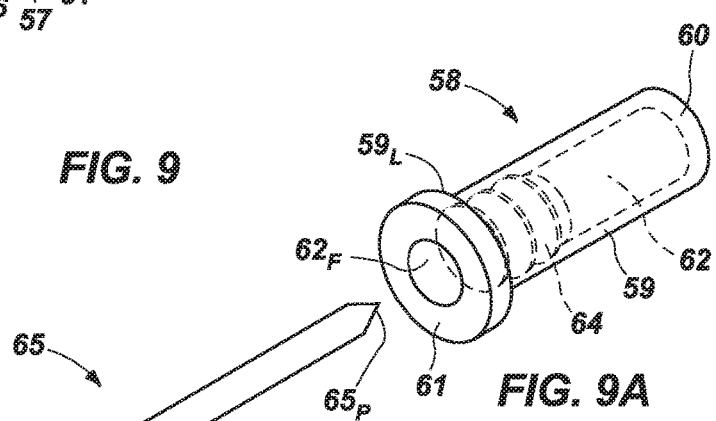
FIG. 9
FIG. 9A
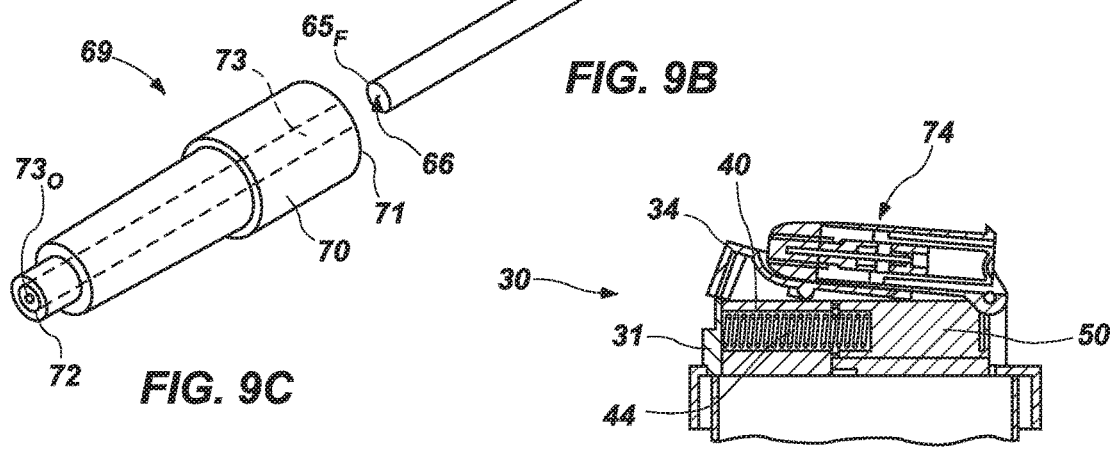
FIG. 9B
FIG. 9C
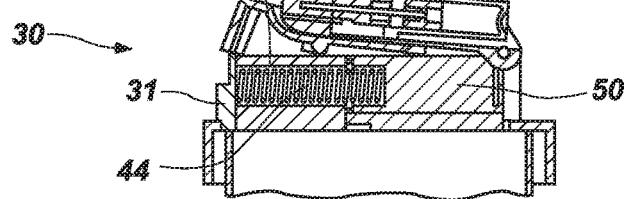
FIG. 10

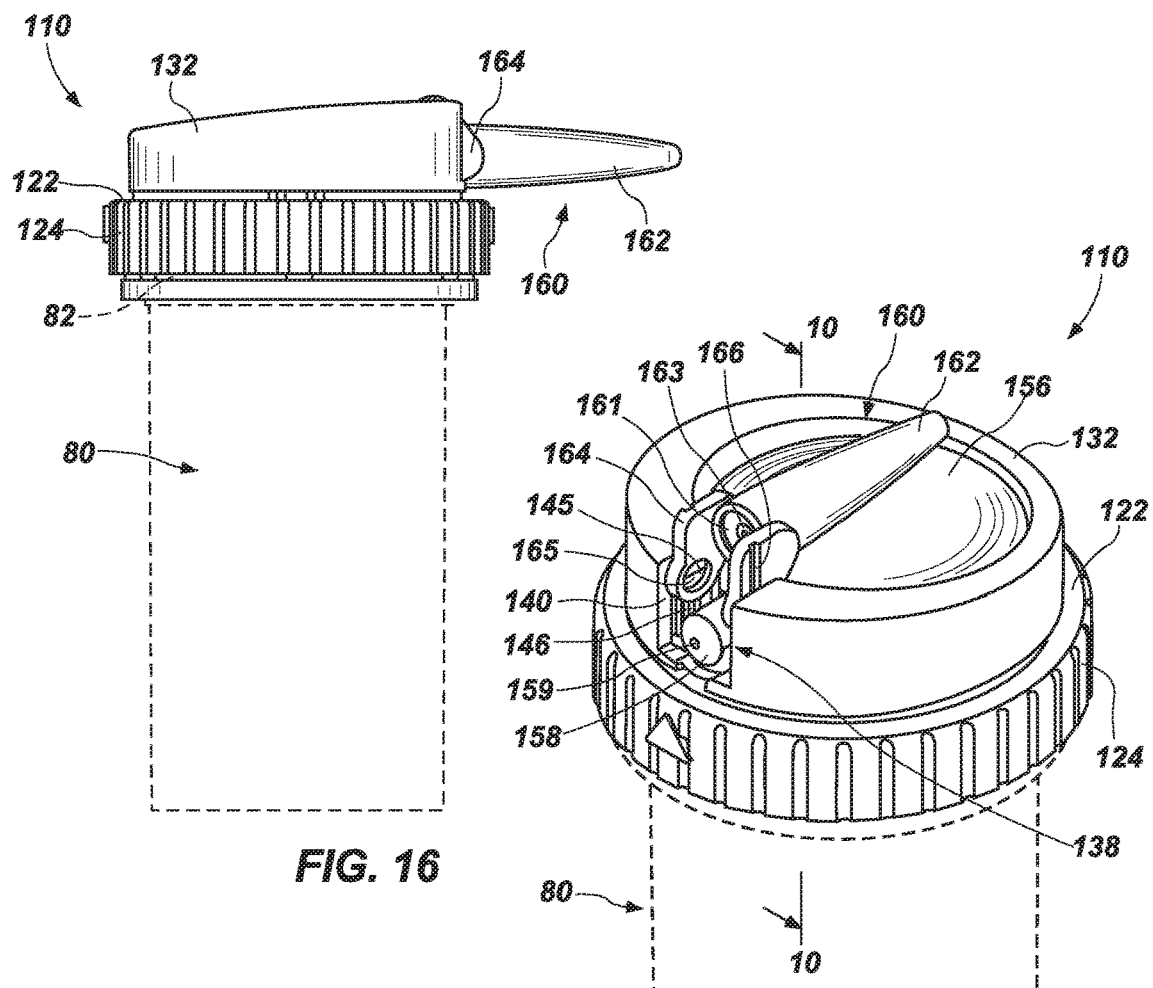
FIG. 16
FIG. 18
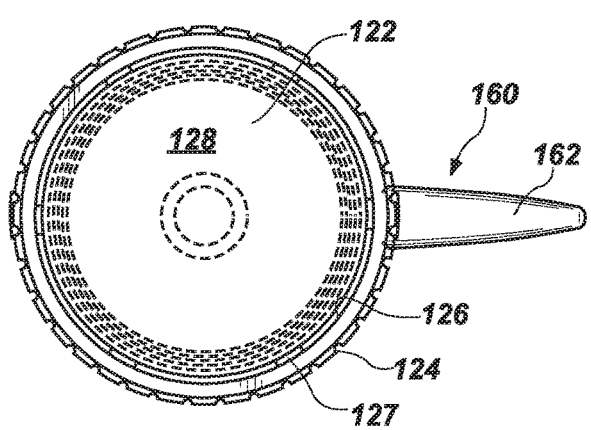
FIG. 17

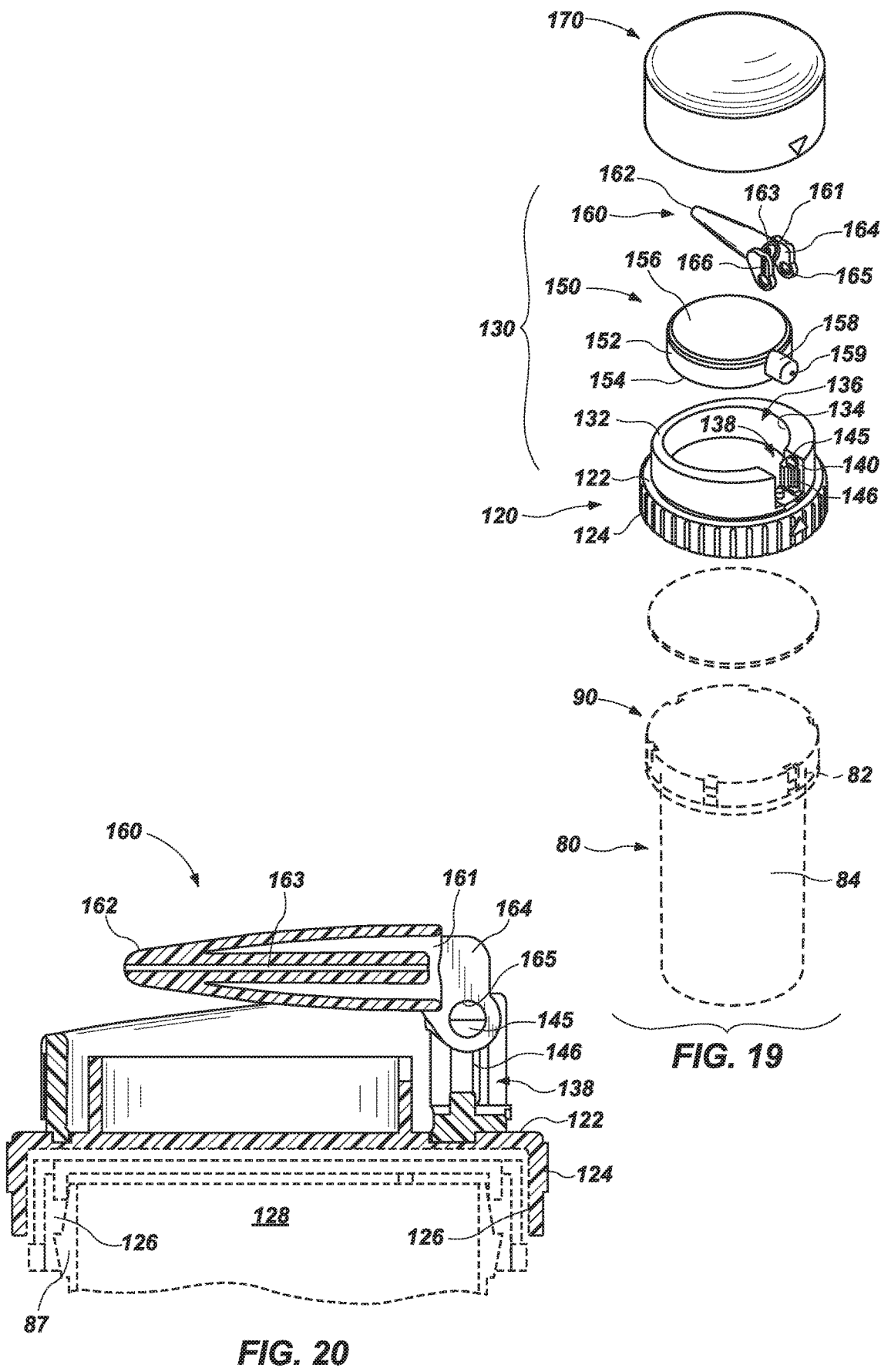

PRESCRIPTION BOTTLE CAP CAPABLE OF ADMINISTERING OPIOID OVERDOSE REVERSAL AGENT

CROSS-REFERENCE TO RELATED APPLICATION

A claim for priority to the Jun. 1, 2017 filing date of U.S. Provisional Patent Application No. 62/513,768, titled NASAL SPRAY DISPENSER CAP ("the '768 Provisional Application") is hereby made pursuant to 35 U.S.C. § 119(e). The entire disclosure of the '768 Provisional Application is hereby incorporated herein.

TECHNICAL FIELD

This disclosure relates generally to prescription bottles and, more specifically, to caps for prescription bottles. More specifically, this disclosure relates to devices that are capable of being used with prescription bottle caps to contain and deliver therapeutic agents, including emergency opioid overdose reversal agents, to an individual in connection with a drug that has been prescribed to the individual. Such a device may include features that enable nasal delivery of therapeutic agents. Methods for providing an individual with a prescription are also disclosed.

RELATED ART

Due to their effectiveness in treating pain, physicians and other licensed healthcare professionals have commonly prescribed opioids used to their patients. While the benefits of opioids have led to their widespread use, they are also highly addictive, and can be dangerous. Oftentimes, a healthcare professional may prescribe an opioid to a patient without realizing the patient suffers from an opioid addiction. A pharmacist may then fill the prescription without any suspicion that the patient suffers from an addition.

While the risks that an individual who suffers from an opioid addition will overdose on opioids are greater than the risks associated with patients who benefit from but are not dependent on opioids, there is always a risk that a recipient of opioids will overdose. That risk has become so significant in recent years that fatalities from opioid overdoses have recently reached epidemic proportions.

Although opioid overdoses can be effectively treated with opioid overdose reversal agents, such as naloxone, access to effective treatments is limited primarily to emergency medical personnel. Because opioid overdoses are often unexpected, and because of the limited availability of countermeasures, unnecessary deaths from opioid overdoses are frequent.

SUMMARY

Apparatuses, systems, and methods for administering therapeutic agents or other substances that correspond to prescribed drugs are disclosed. These include apparatuses, systems, and methods for treating, or reversing the effects of, opioid overdoses.

An apparatus that enables reversal of the effects of an opioid overdose may have a configuration that enables it to be secured to a cap for a prescription bottle, or the apparatus may comprise a cap for a prescription bottle. Accordingly, such an apparatus is referred to herein as a "cap." In addition to including features that enable the cap to contain the contents of the prescription bottle (e.g., an opioid, etc.) within the interior of the prescription bottle, the cap includes a delivery element capable of storing and selectively administering a substance (e.g., a therapeutic agent, such as an opioid overdose reversal agent, etc.) to an individual.

The delivery element of a cap according to this disclosure may be capable of delivering a substance for nasal administration to an individual. Such a delivery element may include a reservoir, a pump, and a nozzle. The reservoir may store the substance. The pump may be capable of forcing the substance from the reservoir, through the nozzle, and out of the nozzle. In some embodiments, the pump may include an actuator that enables an individual to operate the delivery element (e.g., the actuator may be depressible, such as by a finger or thumb of an individual, etc.). The nozzle may be capable of delivering the substance to an individual in a desired manner (e.g., by creating a fine mist from a liquid substance for nasal administration, by creating a puff of a solid substance for nasal administration, etc.). The nozzle of such a delivery element may be movable between a stored orientation and a deployed orientation. While in the stored orientation, the nozzle may be compactly assembled with a remainder of the delivery element. The stored orientation of the nozzle may prevent or preclude use (e.g., depression, etc.) of the actuator of the pump. In its deployed orientation, the nozzle may protrude from the remainder of the delivery element in a manner that facilitates its use in administering the substance to an individual.

In another aspect, drug delivery systems are disclosed. A drug delivery system may include a cap according to this disclosure, as well as a prescription bottle. The prescription bottle may contain a quantity of a first substance, while the cap may contain a quantity of a second substance. The second substance may correspond to the first substance. As an example, the second substance may complement the first substance. As another example, the second substance may counteract a negative effect (e.g., an adverse condition, etc.) caused by the first substance. In embodiments where the first substance is an opioid (e.g., a prescribed opioid, etc.) and the second substance is an opioid overdose reversal agent, a drug delivery system according to this disclosure may facilitate a prompt, effective response to an overdose of the opioid.

According to another aspect, methods for providing prescription drugs, including, but not limited to opioids, to an individual are disclosed. Such a method includes filling a prescription bottle with the prescribed drug and enclosing the prescribed drug within an interior of the prescription bottle with a cap that contains and that is capable of delivering, or administering, a substance that corresponds to the prescribed drug.

A method for administering a substance to an individual to supplement or counteract another substance consumed by the individual includes delivering the substance from a cap of a prescription bottle that contained the consumed substance.

Other aspects of the disclosed subject matter, as well as features and advantages of various aspects of the disclosed subject matter, will become apparent to those of ordinary skill in the art through consideration of the ensuing description, the accompanying drawings, and the appended claims.

BRIEF DESCRIPTION OF THE DRAWINGS

In the drawings:

FIG. 9 is an exploded view of the prescription bottle cap shown in FIG. 1;

FIGS. 9A-9C provide enlarged views of various elements of the prescription bottle cap shown in FIG. 9;

FIG. 10 is a cross-sectional view taken along line 10-10 of FIG. 8 through a centerline of the prescription bottle cap of FIG. 1, including the nozzle of the delivery element of the prescription bottle cap;

FIG. 16 is a right side view of the prescription bottle cap shown in FIG. 11;

FIG. 17 is a bottom view of the prescription bottle cap shown in FIG. 11;

FIG. 18 is a frontal perspective view of the embodiment of prescription bottle cap shown in FIG. 11, with the nozzle of the delivery element in a stored orientation over the actuator of the pump of the delivery element, restricting access to and use of the actuator;

FIG. 19 is an exploded view of prescription bottle cap shown in FIG. 11; and

FIG. 20 is a cross-sectional view taken along line 10-10 of FIG. 18 through a centerline of the prescription bottle cap of FIG. 1, including the nozzle of the delivery element of the prescription bottle cap.

DETAILED DESCRIPTION

FIGS. 1-10 illustrate an embodiment of a prescription bottle cap 10 that can dispense a precise dosage of a substance, and that may be used with a conventional prescription pill dispensing bottle. For the sake of simplicity, the prescription bottle cap may also be referred to herein as a "cap 10" and the conventional prescription pill dispensing bottle may also be referred to herein as a "prescription bottle 80."

Figure 1:
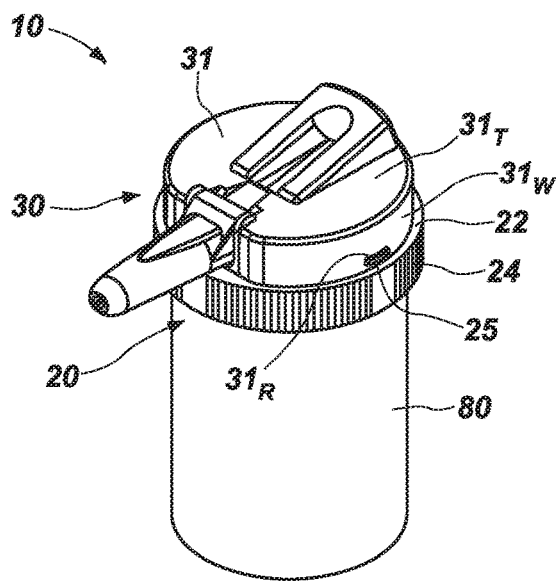
FIG. 1 is a frontal perspective view of an embodiment of a prescription bottle cap, showing a nozzle of a delivery element in a deployed orientation, in which the nozzle protrudes or extends from a remainder of the prescription bottle cap, rendering an actuator of a pump of the delivery element accessible for operation of the delivery element.
Figure 2:
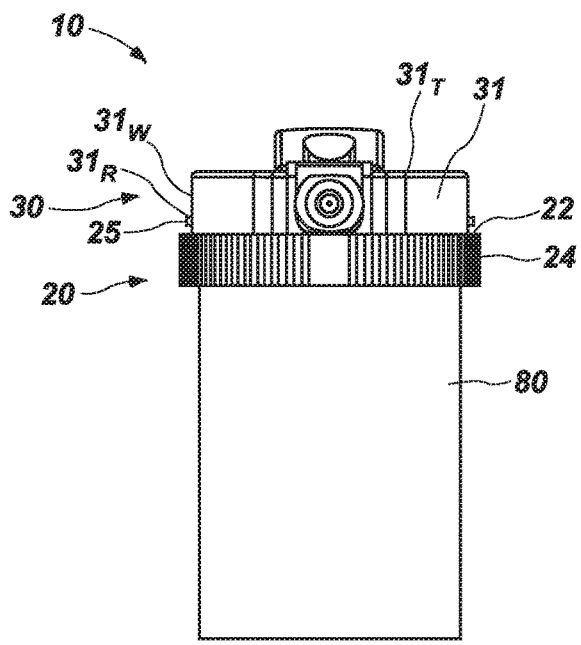
FIG. 2 is a front view of the prescription bottle cap shown in FIG. 1.
Figure 3:
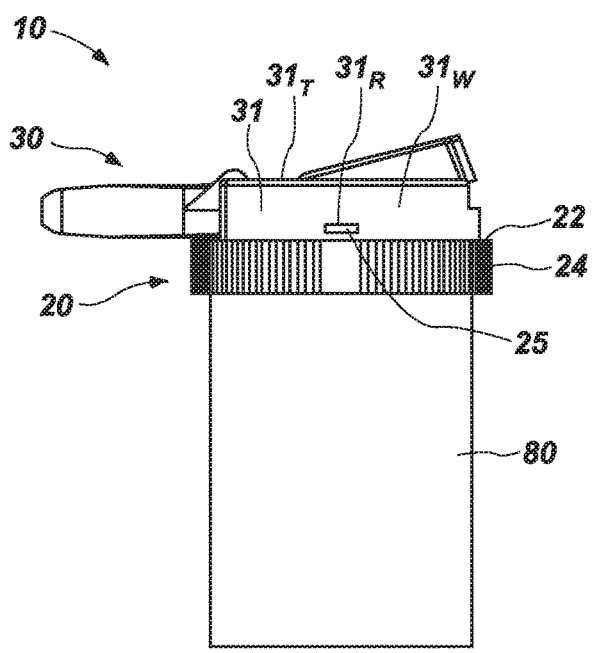
FIG. 3 is a left side view of the prescription bottle cap shown in FIG. 1.
Figure 4:
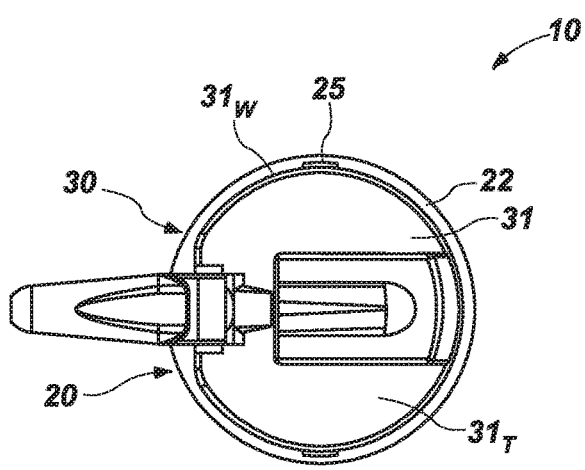
FIG. 4 is a top view of the prescription bottle cap shown in FIG. 1.
Figure 5:
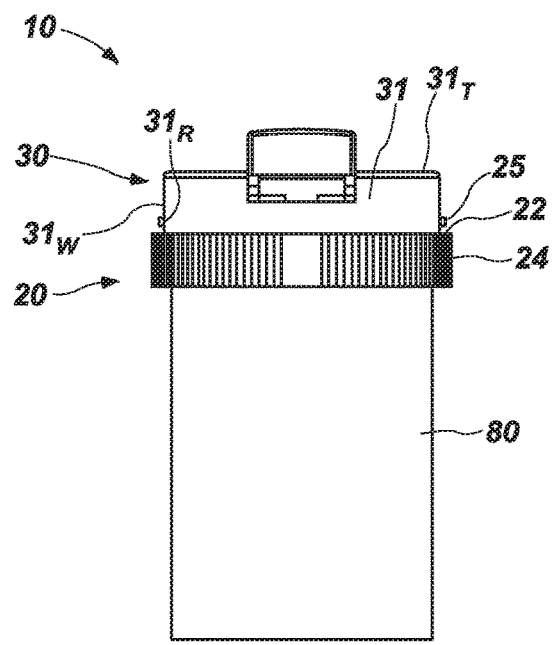
FIG. 5 is a rear view of the prescription bottle cap shown in FIG. 1.
Figure 6:
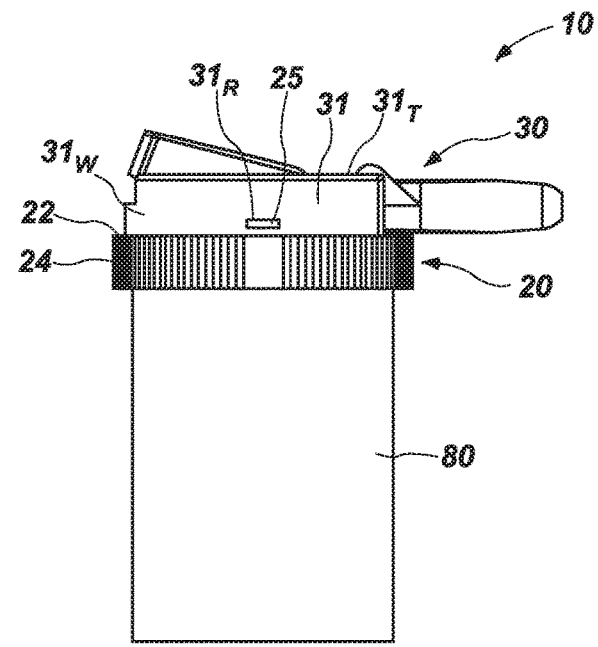
FIG. 6 is a right side view of the prescription bottle cap shown in FIG. 1.
Figure 7:
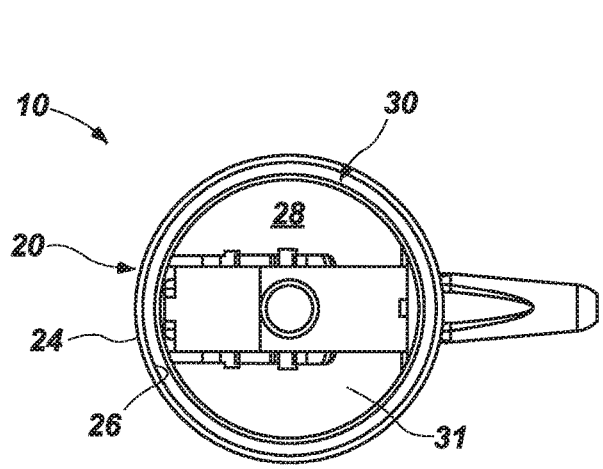
FIG. 7 is a bottom view of the prescription bottle cap shown in FIG. 1.

The cap 10 includes a base 20 and a delivery element 30 atop the base 20. As depicted by FIGS. 1-10, the base 20 of the cap 10 may have a configuration that enables the base 20 to be secured directly to a prescription bottle 80. In such an embodiment, the base 20 may include a top 22 with an outer wall 24 protruding downward from an outer periphery of the top 22. As shown in FIGS. 7 and 10, an inner surface 26 of the outer wall 24 of the base 20 defines the lateral extent of a receptacle 28 capable of receiving an upper portion (not shown) of an outer wall (not shown) of the prescription bottle 80, and bottle coupling features (not shown) on the inner surface 26 of the outer wall 24 of the base 20. The bottle coupling features are complementary to and capable of engaging corresponding cap coupling features (not shown) at the upper portion of the prescription bottle 80 to enable the cap 10 to be secured to the prescription bottle 80. The bottle coupling features of the cap 10 and the cap coupling features of the prescription bottle 80 may have any suitable configurations known in the art. In a specific embodiment, the cap 10 may comprise a conventional child-resistant prescription bottle cap.

Alternatively, the base 20 of the cap 10 may have a configuration that enables it to be attached to a conventional cap for a prescription bottle 80. As an example, the outer wall 24 of the base 20 may define a receptacle 28 that is capable of receiving and engaging a conventional cap (not shown) for a prescription bottle 80 (e.g., mechanically (e.g., by way of a snap fit, a press fit, a threaded engagement, etc.), adhesively, etc.).

The delivery element 30 is capable of delivering, or administering, a substance to an individual. In some embodiments, such as that depicted by FIGS. 1-10, the delivery element 30 of the cap 10 may be capable of nasal delivery, or administration, of a substance to an individual.

With continued reference to FIGS. 1-10, the delivery element 30 of the cap 10 may include a delivery element housing 31 that is secured to the top 22 of the base 20 of the cap 10. The delivery element housing 31 may include a top $31_T$ with an outer wall $31_W$ protruding downward from an outer periphery of the top $31_T$. As depicted by FIGS. 1-6, 8, and 9, apertures or other receptacles $31_R$ in an interior surface (not shown) of the outer wall $31_W$ of the delivery element housing 31 may receive complementary engagement elements 25 that include features that protrude radially outward above the top 22 of the base 20 to enable the delivery element housing 31 to mechanically engage the base 20.

As best illustrated by FIGS. 9 and 10, the delivery element housing 31 may carry a remainder of the delivery element 30. A trigger receptacle 32 may open to the top $31_T$ of the delivery element housing 31 and to a rear portion of the outer wall $31_W$ of the delivery element housing 31, while a nozzle receptacle 33 may comprise an opening in a front portion of the outer wall $31_W$ of the delivery element housing 31, and extend into the top $31_T$ of the delivery element housing 31.

With reference to FIGS. 9, 9A, 9B, 9C, and 10, the remainder of the delivery element 30 includes a trigger 34, a spring housing 40, a compression spring 44, a piston 45, a piston housing 50, an ampoule 58, a needle 65, a needle housing 69, and a nozzle 74.

The spring housing 40 is positioned within the delivery element housing 31, just below the trigger receptacle 32. An upper portion of the spring housing 40 is exposed to and is accessible from the trigger receptacle 32. A body 41 of the spring housing 40 may be coupled to an interior portion of the outer wall 31$_W$ of the delivery element housing 31 in a manner that fixes the spring housing 40 securely in place within the delivery element housing 31, below the trigger receptacle 32. Pivot pins 42 that protrude from opposite sides of the body 41 of the spring housing 40 are aligned with each other and may also be accessible through the trigger receptacle 32.

The trigger 34 has a configuration that enables it to be positioned over and to receive an upper portion of the spring housing 40. As illustrated, the trigger 34 may include a pair of side walls 35 that are spaced apart from one another a sufficient distance that the trigger 34 can receive upper portions of the spring housing 40 and the piston housing 50. A pivot pin receptacle 36 is recessed in a bottom edge 35$_E$ of each side wall 35 of the trigger 34. Each pivot pin receptacle 36 has a configuration that enables it to receive and engage a pivot pin 42 of the spring housing 40 in a manner that secures the trigger 34 atop the spring housing 40 and that enables the trigger 34 to pivot relative to the spring housing 40.

In addition, a catch 37 is recessed in the bottom edge 35$_E$ of each side wall 35 of the trigger 34, near a front edge 35$_F$ of that side wall 35. The catches 37 may be aligned with one another. The catches 37 may hold the piston 45 of the delivery element 30 in a cocked position, as will become apparent from the description that follows. Bottom portions of the front edges 35$_F$ of the side walls 35 may taper from the front of the trigger 34 toward the rear of the trigger 34, or inwardly, to enable the piston 45 of the delivery element 30 to be reset, or re-cocked, while the trigger 34 is depressed, as will become apparent from the description that follows.

Figure 8:
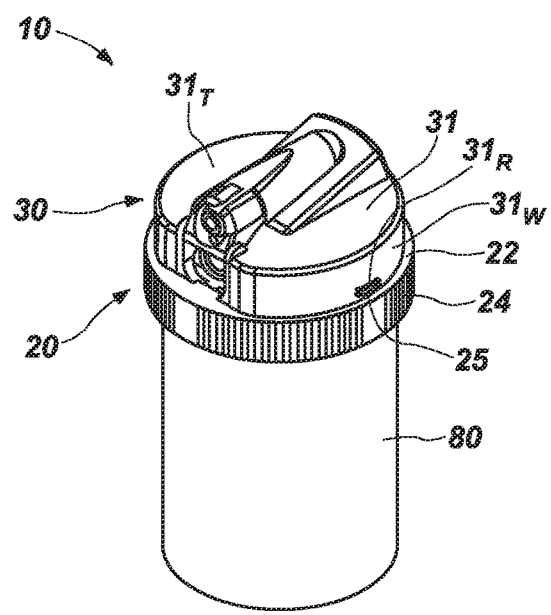
FIG. 8 is a frontal perspective view of the embodiment of prescription bottle cap shown in FIG. 1, with the nozzle of the delivery element in a stored orientation over the actuator of the pump of the delivery element, restricting access to and use of the actuator.
Figures 11, 12:
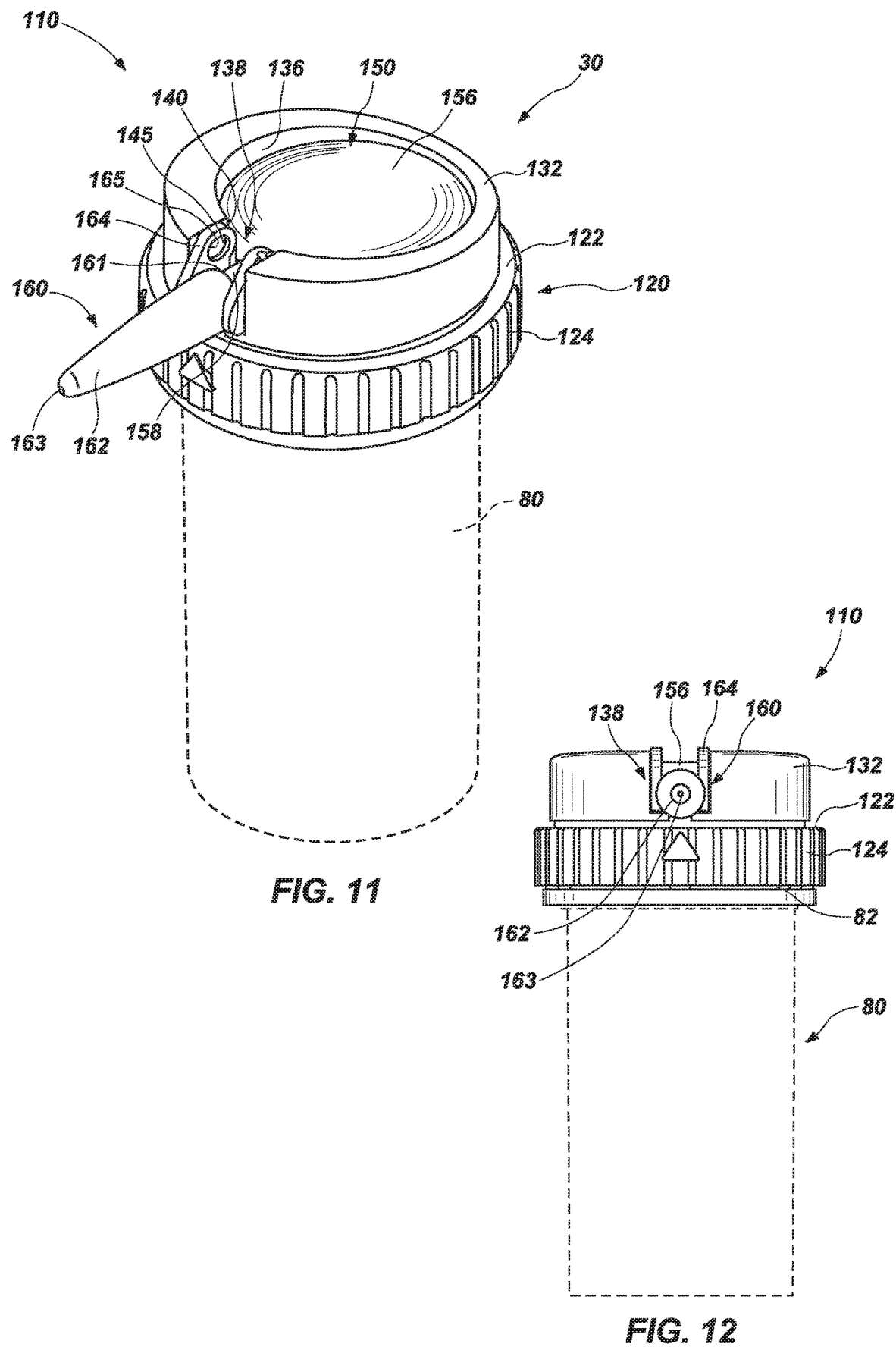
FIG. 11 is a frontal perspective view of an embodiment of a prescription bottle cap, showing a nozzle of a delivery element in a deployed orientation, in which the nozzle protrudes or extends from a remainder of the prescription bottle cap, rendering an actuator of a pump of the delivery element accessible for operation of the delivery element.
FIG. 12 is a front view of the prescription bottle cap shown in FIG. 11.
Figure 13:
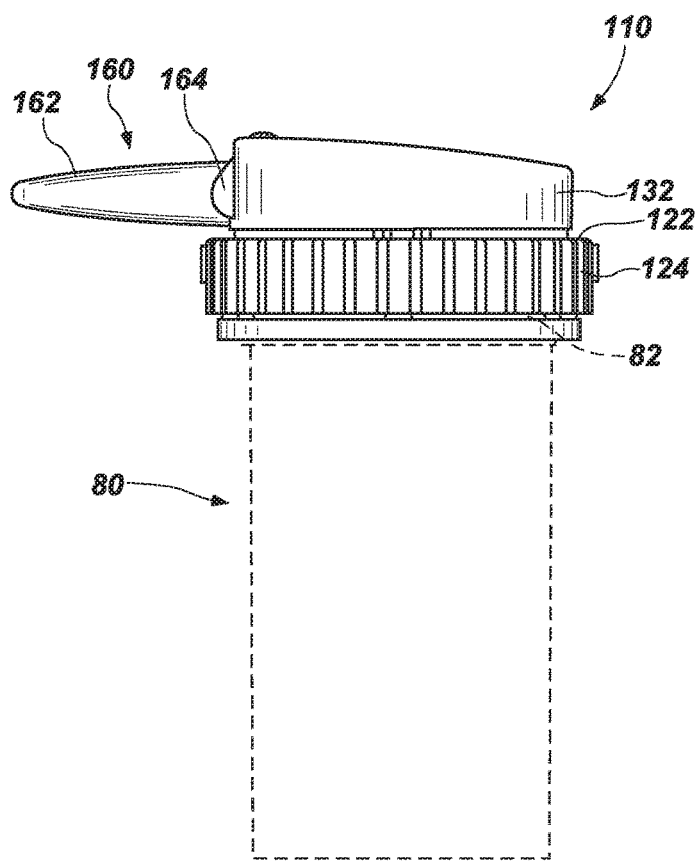
FIG. 13 is a left side view of the prescription bottle cap shown in FIG. 11.
Figure 15:
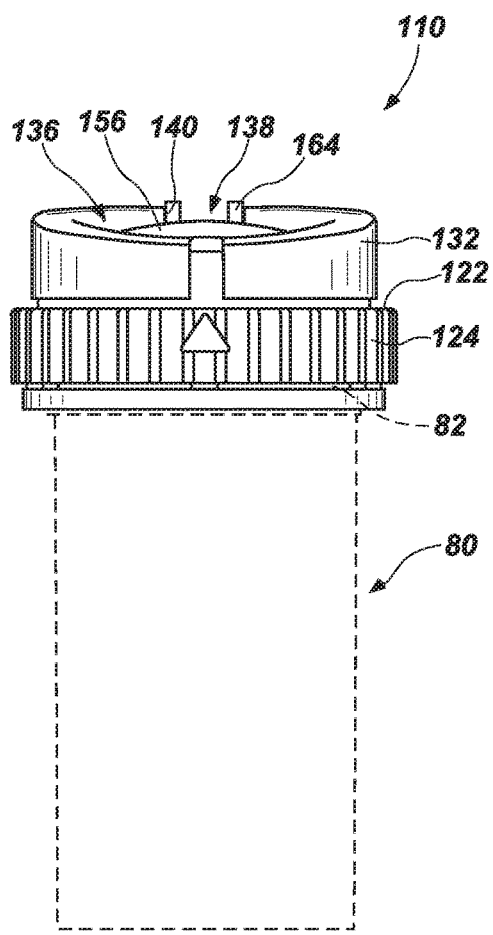
FIG. 15 is a rear view of the prescription bottle cap shown in FIG. 11.
Figure 14:
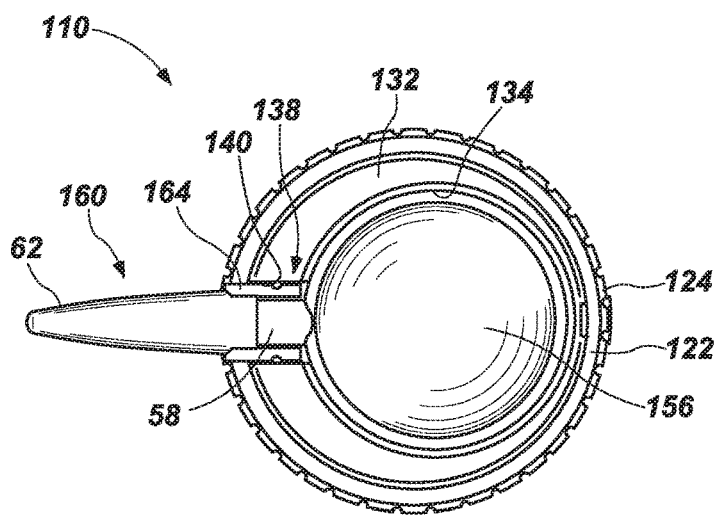
FIG. 14 is a top view of the prescription bottle cap shown in FIG. 11.

When the trigger 34 is assembled with the spring housing 40, the trigger 34 may protrude through the trigger receptacle 32 of the delivery element housing 31. A nozzle receptacle 38 in a top surface 34$_T$ of the trigger 34 may have a configuration that enables the nozzle receptacle 38 to receive the nozzle 74 of the delivery element 30, when folded over the trigger 34, as shown in FIGS. 8 and 10, to pivot the trigger 34 forward (i.e., the orientation of the trigger 34 that enables the piston 45 of the delivery element 30 to be cocked) and to prevent depression of the trigger 34.

Returning reference to the spring housing 40, a bore 43 extends into a front end 41$_F$ of the body 41 of the spring housing 40. While a front end 43$_F$ of the bore 43 is open, a rear end (not shown) of the bore 43 is partially closed (e.g., has a smaller diameter than the front end 43F, is partially blocked, etc.) or completely closed. The bore 43 has a shape and dimensions that enable it to receive the compression spring 44, with a rear end 44$_R$ of the compression spring 44 abutting the rear end of the bore 43. The compression spring 44 may have a length that enables is to reside completely within the bore 43 when compressed and protrude from the open end of the bore 43 when relaxed. The compression spring 44 may have a configuration that enables it to exert a desired amount of force when a compressive force on the compression spring 44 is released.

The piston 45 of the delivery element 30 is positioned in front of the spring housing 40 and in front of the compression spring 44. The piston 45 includes a body 46 with a rear end 47 that abuts a front end 44$_F$ of the compression spring 44. A pair of guides 48 protrude from opposite sides of the body 46, and are capable of being engaged by the catches 37 in the bottom edges 35$_E$ of the side walls 35 of the trigger 34.

A front end 49 of the body 46 of the piston 45 has a configuration that enables it to abut and apply force to a rear portion of the ampoule 58, which may also be referred to as a "reservoir."

The piston housing 50 may have a configuration that enables it to guide movement of the piston 45 as the compression spring 44 forces the piston 45 forward. The piston housing 50 may be positioned within the delivery element housing 31, with a front portion of the piston housing 50 being exposed by the nozzle receptacle 33 of the delivery element housing 31. A rear portion of the piston housing 50 may be exposed to the trigger receptacle 32. A body 51 of the piston housing 50 may be coupled to an interior of the delivery element housing 31 in a manner that fixes the piston housing 50 securely in place within the delivery element housing 31.

In the embodiment illustrated by FIG. 9, a channel 50$_C$ extends through an entire length of the body 51 of the piston housing 50. The channel 50$_C$ has dimensions that enable it to receive the front end 49 of the body 46 of the piston 45. In addition, a horizontally oriented slot 52 extends from a rear end 53 of the body 51 to a location near, but short of, the front end 54 of the body 51. The horizontally oriented slot 52 intersects the channel 50$_C$, enabling the horizontally oriented slot 52 to accommodate the guides 48 that protrude from opposite sides of the piston 45 as the body 46 of the piston 45 is inserted into the channel 50$_C$ through the rear end 53 of the body 51. Together, the horizontally oriented slot 52 and the guides 48 limit forward travel of the piston 45, which may prevent damage to the needle 65.

The partial positioning of the rear portion of the piston housing 50 below a front portion of the trigger receptacle 32 enables the catches 37 in the bottom edges 35$_E$ of the side walls 35 of the trigger 34 to engage portions of the guides 48 that protrude from sizes of the body 51 of the piston housing 50 when the rear end 47 of the piston 45 is pulled against the front end 41$_F$ of the spring housing 40 and, thus, while the compression spring 44 is compressed within the bore 43 of the spring housing 40 and the guides 48 are located near a rear end of the horizontally oriented slot 52.

The front portion of the piston housing 50 includes arms 56. The arms 56, which located on opposite sides of the body 51 of the piston housing 50, are spaced apart from one another, may comprise extensions of the side walls 51$_W$ of the body 51. More specifically, each arm 56 may comprise a vertically oriented structure that extends forward beyond the surface 55 at the front end 54 of the body 51, to which the channel 50$_C$ opens, and upward beyond a top surface 51$_T$ of the body 51. An upper portion 56$_U$ of each arm 56 may include a pivot point 57, such as an aperture that may receive a pivot pin.

As indicated previously herein, a front portion of the piston housing 50, including the front end 54 and front surface 55 of the body 51 of the piston housing 50, as well as the arms 56 of the piston housing 50, is exposed through the nozzle receptacle 33 that opens to the front of the delivery element housing 31. Thus, when the piston housing 50 is assembled with the delivery element housing 31, the channel 50$_C$ of the piston housing 50 is exposed through the nozzle receptacle 33. Outer surfaces of the arms 56 may abut side edges of the nozzle receptacle 33, while the upper portion 56$_U$ of each arm 56 may extend beyond a top 31$_T$ of the delivery element housing 31, which may position the pivot point 57 of each arm 56 above the top 31$_T$ of the delivery element housing 31.

Referring again to the ampoule 58, which is also illustrated by FIG. 9A, a rear end 60 of a body 59 of the ampoule 58 can be removably received within the channel $50_C$ of the piston housing 50. A lip $59_L$ may be provided at the front end 61 of the body 59 to limit a distance the ampoule 58 may be inserted into the channel $50_C$ of the piston 45.

The body 59 of the ampoule 58 defines a reservoir 62, which opens to a front end 61 of the body 59. The reservoir 62 is capable of receiving and containing a single of a drug or another substance. The drug or other substance may be in liquid form (e.g., naloxone, etc.) A stopper 64 may be positioned within a front end $62_F$ of the reservoir 62 holds that substance within the reservoir 62. The stopper 64 may have a configuration that enables it to provide access to the contents of the reservoir 62 when the stopper 64 is subjected to a sufficient force (e.g., that provided by the compression spring 44 and the piston 45, etc.). As an example, the stopper 64 of the ampoule 58 may have a configuration (e.g., a shape, dimensions, a material, etc.) that enables it to be pierced by a needle 65, such as that shown in FIG. 9B, when the compression spring 44 and the piston 45 force the stopper 64 against a piercing end $65_P$ of the needle 65. In addition, a configuration of the stopper 64 may enable it to be forced rearwardly into the reservoir 62 to enable a precise dose of the contents of the reservoir 62 to be forced into a lumen 66 of the needle 65 (and, thus, to be administered to an individual). Such rearward movement of the stopper 64 through the reservoir 62 may cause all of the contents of the reservoir 62 to be ejected through the lumen of the needle 65. By way of example only, the stopper 64 may be formed from an elastomer that may be pierced by the needle 65 and forced rearwardly through the reservoir 62 by a portion of the needle housing 69 while providing a seal against the interior surfaces of the reservoir 62.

The substance within the reservoir 62 of the body 59 of the ampoule 58 may correspond to a drug within the prescription bottle 80 with which the cap 10 is to be used. In some embodiments, the substance may counteract a potentially negative effect (e.g., an overdose, a side effect, etc.) of that drug. As a non-limiting example, when the prescription bottle 80 bottle contains an opioid, the substance within the reservoir 62 of the body 59 of the ampoule 58 may counteract an overdose of the opioid. More specifically, the substance may comprise the narcotic counteragent naloxone. In other embodiments, the substance within the reservoir 620 of the body 59 of the ampoule 58 may complement or act synergistically with the drug contained by the prescription bottle 80 with which the cap 10 is to be used.

The cap 10 may be provided with a plurality of ampoules 58. When the cap 10 is used with a prescription bottle 80 that contains a prescription for an opioid, it may be provide with two ampoules 58, each containing an emergency dose of naloxone.

A front end $65_P$ and a portion of the length of the needle 65 may be retained by the needle housing 69, an embodiment of which is depicted by FIGS. 9 and 9C, with the piercing end $65_P$ of the needle 65 protruding beyond a rear end 71 of a body 70 of the needle housing 69. More specifically, a lumen 73 through the body 70 may receive a front portion of the needle 65. An orifice $73_O$ at a front end of the lumen 73, which opens to a front end 72 of the body 70, may be constricted to limit forward movement of the needle 65 relative to the needle housing 69. The orifice $73_O$ may be configured to atomize a substance (e.g., the contents of the reservoir 62 of the ampoule 58, etc.) as the substance is forced out of the lumen 66 (FIG. 9B) of the needle 65 and through the orifice $73_O$.

The body 70 of the needle housing 69 may have a configuration that enables it to be received by a receptacle (not shown) that opens to a rear end 76 of a body 75 of the nozzle 74. The receptacle in the rear end 76 of the body 75 of the nozzle 74 may also have a configuration that enables it to receive the front end 61 of the body 59 of the ampoule 58 as the piston 45 forces the ampoule 58 forward onto the needle 65.

The body 75 of the nozzle 74 may be tapered to facilitate is insertion into a nostril of an individual to whom a dose of the contents of the ampoule 58 are to be administered. An orifice 79 in a tip 78 of the body 75 communicates with the orifice $73_O$ of the needle housing 69; thus, a substance that is ejected through the orifice $73_O$ of the needle housing 69 may pass through the orifice 79 in the tip 78 of the body 75 of the nozzle 74.

At its rear end 76, the body 75 of the nozzle 74 may include a hinge element $75_H$, which may extend somewhat upwardly and/or rearwardly from the rear end 76 of the body 75. A configuration of the hinge element $75_H$ may enable it to be positioned between the arms 56 of the piston housing 50. A pivot point 77 of the hinge element $75_H$ may align with the pivot points 57 of the arms 56 in a manner that enables the nozzle 74 to be pivotally coupled to the piston housing 50 (e.g., with a pivot pin that extends through the aligned pivot points 57 and 77, etc.).

The pivotal relationship between the nozzle 74 and the piston housing 50 and, thus, between the nozzle 74 and the remainder of the cap 10 enables movement of the nozzle 74 between a stored orientation, in which the nozzle 74 is positioned over the trigger 34 (as depicted by FIGS. 8 and 10) and a deployed orientation, in which the nozzle 74 may protrude from a remainder of the cap 10 (as depicted by FIGS. 1-7) and can communicate with an ampoule 58 that has been inserted into the channel $50_C$ of the piston housing 50. In the depicted embodiment, the nozzle 74 pivots about 180° between its stored orientation and its deployed orientation.

When the nozzle 74 is in its stored orientation, it may partially rest within the nozzle receptacle 33 of the trigger and may preclude access to and/or prevent depression of the trigger 34. When the nozzle 74 is in its deployed orientation, the rear end 76 of its body 75, the rear end 71 of the body 70 of the needle housing 69, and the piercing end $65_P$ of the needle 65 may be positioned adjacent to or against the front end 54 of the body 51 of the piston housing 50 and against the front end 61 of the body 59 of an ampoule 58 (if any) disposed within the channel $50_C$ through the piston housing 50. In addition, when the nozzle 74 is in its deployed orientation, the nozzle 74 may protrude from the remainder of the cap 10 in a manner that facilitates its intended use. For example, the tip 78 of the illustrated embodiment of nozzle 74 may be inserted into an individuals' nostril to enable a substance within the reservoir 62 in the body 59 of the ampoule 58 to be forced directly into the individual's nasal cavity. As will be appreciated, the nozzle 74 may be provided in one or more sizes (e.g., infant, child, adult, etc.), depending upon the age of the intended recipient and/or the size of the intended recipient's nostrils.

The base 20, the delivery element housing 31, the spring housing 40, the piston 45, the piston housing 50, and the nozzle 74 may be formed from any suitable material. As an example, polyethylene terephthalate PET(E), a recyclable and durable material, may be used to form any or all of these components. Each of these elements may be formed from any technique suitable for use with the desired material (e.g., by injection molding processes, etc.).

When the contents of an ampoule 58 are needed, an individual who will be administering those contents place the nozzle 74 of a delivery element 30 of a cap 10 in a stored orientation over the trigger 34 of the delivery element 30, hold the trigger 34 down, ensure that the ampoule 58 is properly oriented, and push the properly oriented ampoule 58 into the channel $50_C$ of the piston housing 50. As the ampoule 58 is pushed into the channel $50_C$, it forces the piston 45 back, compressing the compression spring 44 and enabling the guides 48 that protrude from the body 46 of the piston 45 to be engaged by the catches 37 in the bottom edges $35_E$ of the side walls 35 of the trigger 34; thus cocking, or loading, the delivery element 30.

With continued reference to FIGS. 9 and 10, the contents of the ampoule 58 may be administered by pivoting the nozzle 74 to its deployed orientation, as depicted by FIGS. 8 and 10. With the nozzle 74 in its deployed orientation, the trigger 34 is accessible. Once the nozzle 74 has been positioned to deliver the contents of the ampoule 58 (e.g., in a nostril of an individual, etc.), the trigger 34 may be pushed, or depressed. As the trigger 34 is depressed, the catches 37 release the guides 48 of the piston 45, enabling the compression spring 44 to force the piston 45 forward through the piston housing 50. As the piston 45 moves forward through the piston housing 50, it forces the ampoule 58 forward onto the piercing end $65_P$ of the needle 65. The needle 65 and, optionally, a protruding feature of the needle housing 69 hold the stopper 64 in place, causing it to travel further into the reservoir 62 in the body 59 of the ampoule 58 as the ampoule 58 is forced forward. As the stopper 64 is forced further into the reservoir 62, its contents are expelled through the lumen 66 of the needle 65, the orifice 73O of the needle housing 69, and out of the orifice 79 in the tip 78 of the nozzle 74.

Once a dose of the contents of the ampoule 58 have been administered, the depleted, or spent, ampoule 58 may be removed from the delivery element 30, another ampoule 58 may be assembled with the delivery element 30, and the delivery element 30 may be reset, or re-cocked. The nozzle 74 may be placed in its stored orientation over the trigger 34 to enable a depleted ampoule 58 to be removed from the channel $50_C$ of the piston housing 50 and to enable an ampoule 58 that contains a dose of the substance to be placed into the channel $50_C$. The delivery element 30 may then be reset in the manner described above. Once the delivery element 30 has been reset, the second dosage of the substance may be delivered to the subject (e.g., into the individual's other nostril when administering a substance in an attempt to counteract the effects of an opioid, etc.).

When the cap 10 and its contents (or, more specifically, the contents of an ampoule 58 that has been assembled with the cap 10) are used to counteract an opioid overdose by an individual, a person administering the contents of the cap 10 should call emergency services (e.g., 911 in the United States of America, etc.) before administering the contents of the cap 10. The number of doses of counteragent that have been administered to the affected individual should be reported to the emergency responder.

Another embodiment of a prescription bottle cap 110, which may deliver less precise amounts of a substance than the above-described cap 10, is illustrated by FIGS. 11-20. Such a prescription bottle cap 110 may be useful in situations where precise dosages are not critical. The prescription bottle cap 110 may also be referred to as a "cap" 110 for the sake of simplicity. Like the above-described cap 10, the cap 110 may be capable of attachment to a conventional prescription pill dispensing bottle 80, which is also referred to as a "prescription bottle" 80 for the sake of simplicity.

The cap 110 includes a base 120 and a delivery element 130 atop the base 120. In some embodiments, the base 120 of the cap 110 may have a configuration that enables it to be secured directly to a prescription bottle 80. In such an embodiment, the base 120 may include a top 122 with an outer wall 124 protruding downward from an outer periphery of the top 122. As shown in FIGS. 17 and 20, an inner surface 126 of the outer wall 124 of the base 120 defines the lateral extent of a receptacle 128 capable of receiving an upper portion 82 of an outer wall 84 of the prescription bottle 80, and bottle coupling features 127 on the inner surface 126 of the outer wall 124 of the base 120. The bottle coupling features 127 are complementary to and capable of engaging corresponding cap coupling features 87 at the upper portion 82 of the prescription bottle 80 to enable the cap 110 to be secured to the prescription bottle 80. The bottle coupling features 127 of the cap 110 and the cap coupling features 87 of the prescription bottle 80 may have any suitable configurations known in the art. In a specific embodiment, the cap 110 may comprise a conventional child-resistant prescription bottle cap.

Alternatively, the base 120 of the cap 110 may have a configuration that enables it to be attached to a conventional cap for a prescription bottle. As an example, the outer wall 124 of the base 120 may define a receptacle 128 that is capable of receiving and engaging a conventional cap 90 for a prescription bottle 80 (e.g., mechanically (e.g., by way of a snap fit, a press fit, a threaded engagement, etc.), adhesively, etc.).

With continued reference to FIGS. 11-20, the delivery element 130 of the cap 110 is capable of delivering, or administering, a substance to an individual. In some embodiments, such as that depicted by FIGS. 11-20, the delivery element 130 of the cap 110 may be capable of nasal delivery, or administration, of a substance to an individual.

The delivery element 130 of the embodiment of cap 110 depicted by FIGS. 11-20 includes an annular member 132 that protrudes upwardly from the top 122 of the base 120 of the cap 110. As best illustrated by FIGS. 19 and 20, inner surfaces 134 of the annular member 132 and an upper surface of the top 122 of the base 120 may define a receptacle 136 for an atomizer bulb 150 of the delivery element 130.

The atomizer bulb 150 may be configured in a manner known to those of ordinary skill in the art. The atomizer bulb 150 may include a body 152 that comprises a compressible, resilient structure (e.g., it may be formed from a medical grade rubber, etc.). In general, an interior of the body of the atomizer bulb 150 may comprise a reservoir (not shown) capable of receiving and holding a substance (not shown) for potential administration to an individual. As shown in FIG. 19, the atomizer bulb 150 includes an outlet 158 that may communicate with the reservoir, enabling introduction of the substance into the reservoir defined within the body 152 of the atomizer bulb 150 and enabling ejection of the substance from the reservoir. The outlet 158 may protrude from a body 152 of the atomizer bulb 150.

A top of the atomizer bulb 150 may serve as an actuator 156 that is capable of causing a substance within the reservoir of the body 152 of the atomizer bulb 150 to be forced from the reservoir and out of the outlet 158. More specifically, as the actuator 156 of the atomizer bulb 150 is depressed, a volume within the reservoir may decrease, increasing an air pressure within the reservoir and mixing a substance within the reservoir with air and forcing the mixture out of the reservoir through the outlet 158. The atomizer bulb 150 may deliver an approximate dose of the substance when the actuator 156 is depressed.

A base 154 of the body 152 of the atomizer bulb 150 may have a configuration that enables it to seat properly within the receptacle 136 within the annular member 132 of the delivery element 130 of the cap 110 (e.g. the base 154 of the body 152 of the atomizer bulb 150 may be substantially flat, flat, shaped complementarily to a shape of the top 122 of the base 120 of the cap 110, etc.). The body 152 of the atomizer bulb 150 may resiliently engage the inner surfaces 134 of the annular member 132 to removably secure the atomizer bulb 150 within the receptacle 136. Alternatively, or in addition, the base 154 of the body 152 of the atomizer bulb 150 may be affixed within the receptacle 136 with an adhesive material. Without limitation, a removable, pressure sensitive adhesive material may facilitate removal of the atomizer bulb 150 from the receptacle 136 to enable replenishment of the substance within the reservoir of the atomizer bulb 150 after it has been used or once it has reached its expiration date.

The annular member 132 and/or a shape of the atomizer bulb 150 may be capable of ensuring that the atomizer bulb 150 is properly aligned within the receptacle 136 defined by the annular member 132. In the depicted embodiment, the annular member 132 may receive the atomizer bulb 150 in such a way that an outlet 158 of the atomizer bulb 150 extends into a slot 138 defined through a portion of the annular member 132.

The open top of the annular member 132 of the delivery element 130 of the cap 110 enables the atomizer bulb 150 to be assembled with the cap 110, and provides access to the actuator 156 of the atomizer bulb 150. The annular member 132 may taper downward from front to back to further facilitate operation of the actuator 156 with an individual's finger or thumb. While the annular member 132 provides access to the actuator 156, its configuration—it may substantially surround the atomizer bulb 150—and height may prevent inadvertent depression of the actuator 156 and, thus, inadvertent dispensing of substance within the reservoir of the body 152 of the atomizer bulb 150.

In addition to being able to receive the outlet 158 of the atomizer bulb 150 of the delivery element 130 of the cap 110, the slot 138 in the annular member 132 of the delivery element 130 may be capable of orienting a nozzle 160 of the delivery element 130 in such a way that the nozzle 160 can receive and convey a substance ejected by the outlet 158 of the atomizer bulb 150. In addition, the slot 138 may have a configuration that enables it to receive and engage a portion of the nozzle 160. More specifically, the slot 138 may include a pair of opposed end walls 140. Each end wall 140 may include a pivot element 145. In the depicted embodiment, each pivot element 145 comprises a cylindrical protrusion, with pair of pivot elements 145 being opposed to and protruding toward one another. In addition, at least one end wall 140 may include a retention feature 146 that may hold the nozzle 160 in one or more orientations. As depicted, each retention feature 146 may comprise an elongated protrusion.

The pivot elements 145 of the end walls 140 of the slot 138 in the annular member 132 of the delivery element 130 of the cap 110 may engage or be engaged by complementary pivot elements 165 of the nozzle 160. More specifically, the nozzle 160 may include a pair of attachment arms 164 that protrude from opposite sides of a rear end 161 of the nozzle 160. The attachment arms 164 may be spaced apart a sufficient distance to receive the outlet 158 of the atomizer bulb 150. Each attachment arm 164 may include a pivot element 165. In the depicted embodiment, each pivot element 165 comprises a circular aperture that extends through its corresponding attachment arm 164 to receive a cylindrical pivot element 145 that protrudes from a corresponding end wall 140 of the slot 138. When assembled, the pivot elements 145 of the annular member 132 and the pivot elements 165 of the attachment arms 164 of the nozzle 160 function together to enable the nozzle 160 to pivot relative to the annular member 132 of the cap 110 and relative to any atomizer bulb 150 within the receptacle 136 defined by the annular member 132.

In addition to including a pivot element 165, at least one attachment arm 164 may include a retention feature 166 at its outer surface. The retention feature 166 may be configured complementarily to and be able to engage a corresponding retention feature 146 of an end wall 140 of the annular member 132 that defines a side of the slot 138 through the annular member 132. In the depicted embodiment, each retention feature 166 comprises an elongated recess in the outer surface of its attachment arm 164; the elongated recess is capable of receiving the elongated protrusion that forms the corresponding retention feature 146 on the corresponding end wall 140. Such engagement may hold, or retain, the nozzle 160 in one or more orientations.

The pivotal relationship between the nozzle 160 and the remainder of the cap 110 enables movement of the nozzle 160 between a stored orientation, in which the nozzle 160 is positioned over the actuator 156 of the atomizer bulb 150 (as depicted by FIGS. 18 and 20) and a deployed orientation, in which the nozzle 160 can communicate with the outlet 158 of the atomizer bulb 150 and may protrude from a remainder of the cap 110 (as depicted by FIGS. 11-17). In the depicted embodiment, the nozzle 160 pivots about 180° between its stored orientation and its deployed orientation.

The relative arrangements of the retention feature(s) 146 on the end wall(s) 140 of the annular member 132 and the retention feature(s) 166 of the corresponding attachment arm(s) 164 of the nozzle 160 may engage each other to hold the nozzle 160 into place into one or both of the stored orientation and the deployed orientation. The corresponding retention feature(s) 146 and retention feature(s) 166 may be disengaged, and the nozzle 160 pivoted, upon application of a sufficient pivoting force to the nozzle 160 to disengage the corresponding retention feature(s) 146 and retention feature(s) 166.

When the nozzle 160 is in its stored orientation, it may preclude access to and/or prevent depression of the actuator 156 of the atomizer bulb 150. When the nozzle 160 is in its deployed orientation, its rear end 161 may be positioned adjacent to or against an end of the outlet 158 of the atomizer bulb 150, and a channel 163 through the nozzle 160 may be aligned with an aperture 159 of the outlet 158. As can be best seen in FIG. 18, the rear end 161 of the nozzle 160 may be recessed, enabling it to receive an end of the outlet 158 of the atomizer bulb 150 in a manner that ensures alignment of the channel 163 of the nozzle 160 with the aperture 159 of the outlet 158. In some embodiments, the rear end 161 of the nozzle 160 and/or the end of the outlet 158 may be formed from a compressible resilient material or provided with a sealing element (e.g., an O-ring, etc.) to seal the joint between the aperture 159 of the outlet 158 and the channel 163 of the nozzle 160. In addition, when the nozzle 160 is in its deployed orientation, the nozzle 160 may protrude from the remainder of the cap 110 in a manner that facilitates its intended use. For example, a tip 162 of the illustrated embodiment of nozzle 160 may be inserted into an individuals' nostril to enable a substance within the reservoir in the body 152 of the atomizer bulb 150 to be forced directly into the individual's nasal cavity. As will be appreciated, the nozzle 160 may be provided in one or more sizes (e.g., infant, child, adult, etc.), depending upon the age of the intended recipient and/or the size of the intended recipient's nostrils.

As shown in FIG. 19, a safety cap 170 may be provided with the cap 110 to limit access to the delivery element 130 until the delivery element 130 is needed. The safety cap 170 may comprise a conventional snap-on cap that engages features on an outer surface of the annular member 132. A bottom edge of the safety cap 170 may rest on or adjacent to a portion of the top 122 of the base 120 that is exposed beyond an outer periphery of the annular member 132. The safety cap 170 may provide a protective covering for the delivery element 130 of the cap 110 and the substance that within the reservoir within the body 152 of the atomizer bulb 150 of the delivery element 130. A removable seal may secure the safety cap 170 to the remainder of the cap 110.

The base 120, the annular member 132, the nozzle 160, and the safety cap 170 may be formed from any suitable material. As an example, polyethylene terephthalate PET(E), a recyclable and durable material, may be used to form any or all of these components. Each of these elements may be formed from any technique suitable for use with the desired material (e.g., by injection molding processes, etc.).

In some embodiments, the cap 110 may be provided in a sealed wrapper.

In use, the cap 110 may be removed from its prescription bottle 80 (if the cap 110 has not already been removed), a safety cap 170 may be removed from the cap 110 (if the safety cap 170 is assembled with the cap 110), and the nozzle 160 may be pivoted to its deployed orientation. With the nozzle 160 in its deployed orientation, it may be inserted into one of an individual's nostrils. The actuator 158 may then be pressed firmly to force the substance within the reservoir of the body 152 of the atomizer bulb 150 through the nozzle 160 and into the individual's nasal cavity. Once the counteragent has been administered, the nozzle 160 may be removed from the affected individual's nostril. A second dose of the substance may be administered to the individual by replacing the depleted, or spent, atomizer bulb 150 with a fresh atomizer bulb 150, reinserting the nozzle 160 into the individual's other nostril and firmly pressing the actuator 156 of the fresh atomizer bulb 150.

Although the foregoing description sets forth many specifics, these should not be construed as limiting the scope of any of the claims, but merely as providing illustrations of some embodiments and variations of elements or features of the disclosed subject matter. Other embodiments of the disclosed subject matter may be devised which do not depart from the spirit or scope of any of the claims. Features from different embodiments may be employed in combination. Accordingly, the scope of each claim is limited only by its plain language and the legal equivalents thereto.

What is claimed:

1. A cap for a prescription bottle, comprising:
a base capable of being secured to a top of a prescription bottle, the base including a top surface completely covering an opening of the prescription bottle to confine contents of the prescription bottle within an interior of the prescription bottle; and
a delivery element over the top surface of the base, the delivery element including:
a reservoir that contains a substance;
a nozzle in fluid communication with the reservoir, the nozzle moveable between:
a stored orientation in which the nozzle is compactly associated with a remainder of the delivery element; and
a deployed orientation in which the nozzle protrudes from a remainder of the delivery element; and
an actuator that forces the substance from the reservoir, through the nozzle, and out of the nozzle, the actuator including a receptacle for the nozzle that receives the nozzle in the stored orientation to prevent actuation of the actuator, the actuator accessible with the nozzle in the deployed orientation.

2. The cap of claim 1, wherein the delivery element is affixed to a top of the base.

3. The cap of claim 2, wherein the delivery element is integral with the top of the base.

4. The cap of claim 2, wherein the delivery element is capable of being selectively affixed to and/or removed from the top of the base.

5. The cap of claim 1, wherein the substance comprises an opioid overdose reversal agent.

6. The cap of claim 5, wherein the opioid overdose reversal agent comprises naloxone.

7. The cap of claim 1, wherein substance comprises a nasally deliverable drug.

8. The cap of claim 1, wherein the nozzle, while in the stored orientation, prevents depression of the actuator.

9. The cap of claim 1, wherein the nozzle, while in the deployed orientation, protrudes beyond an outer peripheral edge of the delivery element.

10. A drug delivery system, comprising:
a prescription bottle comprising a base, an outer wall protruding upward from an outer periphery of the base to define an interior, and cap coupling features associated with an upper portion of the outer wall; and
a cap, including:
a base including a top, an outer wall protruding downward from an outer periphery of the top to define a receptacle capable of receiving the upper portion of the outer wall of the prescription bottle, and bottle coupling features on an inner surface of the outer wall of the cap, the bottle coupling features of the cap being complementary to and capable of engaging the cap coupling features of the prescription bottle to enable the cap to be secured to the prescription bottle; and
a delivery element atop the base, including:
a reservoir containing a substance;
a nozzle movable between a stored orientation in which the nozzle is compactly associated with a remainder of the delivery element and a deployed orientation in which the nozzle protrudes from a remainder of the delivery element; and
a trigger that forces the substance from the reservoir through the nozzle, the trigger including a recess that receives the nozzle in the stored orientation to prevent depression of the trigger, the trigger exposed and depressible with the nozzle in the deployed orientation.

11. The drug delivery system of claim 10, wherein the delivery element of the cap further includes:
a spring;
a piston capable of being driven forward by the spring, the trigger capable of holding the piston in a loaded position and of releasing the piston to enable the spring to drive the piston forward; and a piston housing including a channel with a rear end capable of receiving the piston and a front end capable of receiving an ampoule comprising the reservoir containing a premeasured dose of a drug, the nozzle capable of positioning a tip of a needle adjacent to a front end of the ampoule to enable the tip of the needle to puncture a stopper of the ampoule and to hold the stopper in place as the piston is driven forward and drives a body of the ampoule forward, the needle capable of receiving and conveying the premeasured dose of the drug to an orifice of the nozzle.

12. The drug delivery system of claim 11, wherein the orifice of the nozzle is capable of atomizing the premeasured dose of the drug.

13. The drug delivery system of claim 11, wherein the interior of the prescription bottle contains an opioid and the ampoule contains an opioid overdose reversal agent.

14. A method for providing a substance to an individual, comprising:

filling a bottle with the substance; and securing a cap to the bottle to secure the substance within the bottle, the cap containing another substance and being capable of readily administering the another substance to the individual, the cap including an actuator and a nozzle, the nozzle movable between a stored orientation in which the nozzle is compactly associated with a remainder of the cap and a deployed orientation in which the nozzle protrudes from the remainder of the cap, the actuator including a receptacle that receives the nozzle in the stored orientation to prevent actuation of the actuator, the actuator exposed and depressible with the nozzle in the deployed orientation.

15. The method of claim 14, wherein securing the cap to the bottle comprises securing a cap with a nozzle and a pump for nasally administering the another substance to the individual to the bottle.

16. The method of claim 14, wherein filling the bottle with the substance comprises filling the bottle with a prescription drug, as prescribed by a licensed medical professional.

17. The method of claim 16, wherein:

filling the bottle with the substance comprises filling the bottle with the prescription drug comprises filling the bottle with an opioid; and securing the cap to the bottle comprises securing the cap with the another substance comprising an opioid reversal agent to the bottle.

\* \* \* \* \*